United States Patent
Malo et al.

(12)

(10) Patent No.: US 6,569,678 B1
(45) Date of Patent: May 27, 2003

(54) PRGR: A POSITIVE SELECTION VECTOR SYSTEM FOR DIRECT CLONING OF PCR AMPLIFIED DNA FRAGMENTS

(75) Inventors: Madhu Sudan Malo, Watertown, MA (US); Zaheed Husain, Medford, MA (US)

(73) Assignee: SyntheGen Systems, Inc., Medford, MA (US)

( * ) Notice: Subject to any disclaimer, the term of this patent is extended or adjusted under 35 U.S.C. 154(b) by 0 days.

(21) Appl. No.: 09/722,219

(22) Filed: Nov. 27, 2000

(51) Int. Cl.[7] .................. C12N 15/63; C12N 15/66; C12N 15/70
(52) U.S. Cl. .................................... 435/320.1
(58) Field of Search ............... 435/320.1, 91.4, 435/91.5, 6, 471, 479

(56) References Cited

U.S. PATENT DOCUMENTS 5,824,469 A * 10/1998 Horwitz et al.
6,284,496 B1 * 9/2001 Litman et al.

OTHER PUBLICATIONS

Robben et al (1995) Protein Engineering 8:159–165.*
Pmll–RO531–NEB Restriction Endonucleases. [online] [retrieved May 16, 2002] Retrieved from the Internet:<URL: www.neb.com/neb/products/res_enzymes/532.html>.*
Bush (2001) Antimicrobial Resistance 32:1085–1089.*
Bush et al (1995) Antimicrobial Agents and Chemotherapy 39:1211–1233.*

* cited by examiner

*Primary Examiner*—Remy Yucel
*Assistant Examiner*—Bronwen M. Loeb
(74) *Attorney, Agent, or Firm*—Ropes & Gray

(57) ABSTRACT

The present invention relates to the development of a positive selection vector based on insertional reconstruction of a reporter gene or of a regulatory gene controlling the expression of a reporter gene. The cloning vector carries a reporter gene or a regulatory gene with a mutation rendering the reporter or the regulatory gene protein functionally inactive. A primer carrying a nucleic acid sequence that corrects the mutation is used during PCR amplification of a targeted nucleic acid sequence, and the amplified DNA fragment is then ligated to the said vector thus reconstructing the wild-type reporter or regulatory gene.

28 Claims, 6 Drawing Sheets

FIG. 2

```
                                                              Not I/Sfi I
                                                       ─────────────────────
5'-CTA AAG TAT ATA TGA GTA AAC TTG GTC TGA CAG CGG CCG CTT AGG CCA
3'-GAT TTC ATA TAT ACT CAT TTG AAC CAG ACT GTC GCC GGC GAA TCC GGT

Cla I/EcoR V   Nde I/Nar I
   ────────────── ───────────
   TCG ATA TCA TAT GGC GCC TTA TTC AAT TAC TAT TCA ACT ATT ATT CAA
   AGC TAT AGT ATA CCG CGG AAT AAG TTA ATG ATA AGT TGA TAA TAA GTT
                              ─────────────────────────────────────
                                          stop codons region Pml I                   Nar I    EcoR V       Nde I
           ───────                  ─────    ──────      ───────
           ** *                       *      *  *         *  *
   TTA CAC GTG CTT AAT CAG TGA GGC GCC GAT ATC AGC CAT ATG TCT ATT
   AAT GTG CAC GAA TTA GTC ACT CCG CGG CTA TAG TCG GTA TAC AGA TAA
       ───

Cla I
                ──────
                  *
   TCG TTC ATC GAT AGT TGC CTG-3'
   AGC AAG TAG CTA TCA ACG GAC-5'
```

FIG. 6

```
                                                               Not I/Sfi I
5'-CTA AAG TAT ATA TGA GTA AAC TTG GTC TGA CAG CGG CCG CTT AGG CCA
3'-GAT TTC ATA TAT ACT CAT TTG AAC CAG ACT GTC GCC GGC GAA TCC GGT

Cla I/EcoR V    Nde I/Nar I         T7 promoter
    TCG ATA TCA TAT GGC GCC TAA TAC GAC TCA CTA TAG TTA TTC AAT TAC
    AGC TAT AGT ATA CCG CGG ATT ATG CTG AGT GAT ATC AAT AAG TTA ATG
                                                    stop codons region Pml I                 Nar I
                                        ** *                  *     *
    TAT TCA ACT ATT ATT CAA TTA CAC GTG CTT AAT CAG TGA GGC GCC GAT
    ATA AGT TGA TAA TAA GTT AAT GTG CAC GAA TTA GTC ACT CCG CGG CTA
            stop codons region EcoR V    Nde I              Cla I
  *       *   *                *
ATC AGC CAT ATG TCT ATT TCG TTC ATC GAT AGT TGC CTG-3'
TAG TCG GTA TAC AGA TAA AGC AAG TAG CTA TCA ACG GAC-5'
```

PRGR: A POSITIVE SELECTION VECTOR SYSTEM FOR DIRECT CLONING OF PCR AMPLIFIED DNA FRAGMENTS

CROSS-REFERENCE TO RELATED APPLICATIONS

References Cited [Referenced by]

U.S. Patent Documents

| | | | |
|---|---|---|---|
| 4683195 | July, 1987 | Mullis et al. | 435/6 |
| 4683202 | July 1987 | Mullis | 435/91 |
| 4965188 | October 1990 | Mullis et al. | 435/6 |
| 5487993 | January 1996 | Herrnstadt et al. | 435/172 |
| 5856144 | January 1999 | Mierendorf et al. | 435/91 |
| 5891687 | April 1999 | Schlieper et al. | 935/172 |
| 5910438 | June 1999 | Bernard et al. | 435/252 |

OTHER REFERENCES

Ahrenhotz et al., "A conditional suicide system in *Escherichia coli* based on intracellular degradation of DNA" Appl. Environ. Microbiol. 60, 3746–3751 (1994).

Altenbuchner et al., "Positive selection vectors based on palindromic DNA sequences" Methods Enzymol. 216, 457–466 (1992).

Bernard et al., "New ccdB positive-selection cloning vectors with kanamycin or chloramphenicol selectable markers" Gene 148, 71–74 (1994).

Bolivar et al., "Construction and characterization of new cloning vehicles, II. A multipurpose cloning system" Gene 2, 95–113 (1977).

Clark, J. M., "Novel non-templated nucleotide addition reactions catalyzed by prokaryotic and eukaryotic DNA polymerases" Nucl. Acids Res. 16, 9677–9686 (1988).

Henrich, B. and Plapp, R., "Use of the lysis gene of bacteriophage phi X174 for the construction of a positive selection vector" Gene 42, 345–349 (1986).

Henrich, B. and Schmidtberger, B., "Positive-selection vector with enhanced lytic potential based on a variant of phi X174 phage gene E" Gene 154, 51–54 (1995).

Holton, T. A. and Graham, M. W., "A simple and efficient method for direct cloning of PCR products using ddT-tailed vectors" Nucl. Acids Res. 19, 1156 (1991).

Hu, G., "DNA polymerase-catalyzed addition of nontemplated extra nucleotides to the 3' end of a DNA fragment" DNA Cell Biol. 12, 763–770 (1993).

Kast, P., "pKSS—a second-generation general purpose cloning vector for efficient positive selection of recombinant clones" Gene 138, 109–114 (1994).

Kaufmann, D. L. and Evans, G. A., "restriction endonuclease cleavage at the termini of PCR products" BioTechniques 9, 304–306 (1990).

Kuhn et al., "Positive selection vectors utilizing lethality of EcoRI endonuclease" Gene 42, 252–263 (1986).

Malo, M. S. and Loughlin, R. E., "Promoter elements and regulation of expression of the cysD gene of *Escherichia coli* K-12" Gene 87, 127–131 (1990).

Mead et al., "Bst DNA polymerase permits rapid sequence analysis from nanogram amounts of template" BioTechniques 9, 657–663 (1991).

Messing et al., "Filamentous coliphage M13 as a cloning vehicle: insertion of a HindII fragment of the lac regulatory region in M13 replicative form in vitro" Proc. Natl. Acad. Sci. 79, 3642–3646 (1977).

Mullis, K. B. and Faloona, F. A., "Specific synthesis of DNA in vitro via polymerase-catalyzed chain reaction" 1987, Methods Enzymol. 155, 335–350 (1987).

Norrander et al., "Construction of improved M13 vectors using oligodeoxynucleotide-directed mutagenesis" Gene 26, 101–106 (1983).

Pierce et al., "A positive selection vector for cloning high molecular DNA by bacteriophage P1 system: improved cloning efficiency" Proc. Natl. Acad. Sci. 89, 2056–2060 (1992).

Sambrook et al., Molecular Cloning: A Laboratory Manual, Cold Spring Harbor Laboratory, Cold Spring Harbor, N.Y. (1989).

Saiki et al., "Enzymatic amplification of beta-globin genomic sequences and restriction site analysis for diagnosis of sickle cell anemia" Science 230, 1350–1354 (1985).

Yanisch-Perron et al., "Improved M13 phage cloning vectors and host strains: nucleotide sequences of the M13mp18 pUC19 vectors" Gene 33, 103–119 (1985).

Yazynin et al., "A plasmid vector with positive selection and directional cloning based on a conditionally lethal gene" Gene 169, 131–132 (1996).

STATEMENT REGARDING FEDERALLY SPONSORED RESEARCHER DEVELOPMENT

Not Applicable

REFERENCE TO A MICROFICHE APPENDIX

Not Applicable

REFERENCE TO SEQUENCE LISTING

Not Applicable

FIELD OF THE INVENTION

The present invention relates to a positive selection vector system for direct cloning of PCR amplified nucleic acids. The invention involves insertional reconstruction of a reporter or of a regulatory gene. The invention describes reduction of exonuclease-induced false positive clones in a cloning experiment.

BACKGROUND OF THE INVENTION

Polymerase chain reaction or PCR (Saiki et al., 1985, Science 230, 1350–1354; Mullis and Faloona, 1987, Method Enzymol. 155, 335–350; U.S. Pat. Nos. 4,683,195; 4,683,202 and 4,965,188) is a milestone technological development in the field of molecular biology and genetic engineering. For amplification of a target nucleic acid PCR uses a polymerase, target sequence-specific forward and reverse primers, deoxynucleotides and a minute amount of target nucleic acid as the template. Repeated cycles of denaturation of double-stranded DNA followed by primer annealing and primer extension achieve an exponential amplification of the target DNA sequence.

The PCR product itself could be used for diagnosis, quantitation of the template, direct sequencing and some other applications (U.S. Pat. Nos. 5,856,144; 5,487,993 and 5,891,687). However, for applications such as mutation analysis, sequencing, gene expression, identification of polymorphic transcripts, making RNA probes etc., usually a large quantity of DNA is needed. Thus it is necessary to isolate a bacterial clone carrying the PCR generated target DNA fragment in a vector. Different methods for cloning PCR generated DNA fragments have been described. One such method involves incorporation of restriction endonuclease cleavage sites near the 5' end of the PCR primers and the PCR product thus obtained is subjected to purification, restriction digestion with the respective endonuclease followed by ligation into a compatible vector, transformation and identification of the bacterial clone carrying the PCR fragment (Kaufmann and Evans, 1990, BioTechniques 9, 304–306).

The most common method for cloning a PCR product utilizes the nontemplate-dependent terminal transferase or extendase activity of Taq DNA polymerase, which usually produces a dAMP (deoxyadenosine monophosphate) overhang at the 3' end of the PCR amplified DNA fragment (Clark, 1988, Nucl. Acid Res. 16, 9677–9686; Hu, 1993, DNA Cell Biol. 12, 763–770). The PCR product thus obtained is ligated into a linearized vector carrying a dTMP (deoxythymidine monophosphate) overhang at the 3' end (U.S. Pat. No. 5,487,993; Mead et al., 1991, BioTechniques 9, 657–663; Holton and Graham, 1991, Nucl. Acids Res. 19, 1156). A similar strategy has been used when Taq polymerase generated PCR fragments carrying dAMP overhang at the 3' end are ligated into a linearized vector carrying an inosine or uracil overhang at the 3' end (U.S. Pat. No. 5,856,144).

The above-mentioned vectors lack the positive selection capability. Thus upon transformation, all host cells carrying either the recombinant vector (containing an insert) or the nonrecombinant vector (containing no insert DNA) grow in the desired medium at an equal growth rate. To differentiate between a host cell carrying only the nonrecombinant vector from the host cell carrying the recombinant vector, DNA fragment is usually inserted into a chromogenic gene, the product of which is inactivated thus rendering the recombinant colony white in a chromogenic medium. When the chromogenic gene is lacZ, the transformant carrying the nonrecombinant vector turns blue in the presence of X-gal, the substrate for the lacZ gene product β-galactosidase (Messing et al., 1977, Proc. Natl. Acad. Sci. 79, 3642–3646; Norrander et al., 1983, Gene 26, 101–106; Yanisch-Perron et al., 1985, Gene 33, 103–119). When the number of recombinant colonies are low and nonrecombinant colonies are high in a plate, then it becomes very difficult to differentiate the recombinant colonies from the non-recombinant colonies. High number of colonies also lead to contamination between the recombinant and nonrecombinant colonies. Insertion of a small DNA fragment sometimes can generate pale blue recombinant clones, which may not be differentiated from the pale blue nonrecombinant clones arising from nonuniform distribution of Xgal, especially when Xgal is spread on the surface of medium.

To ameliorate the problems associated with the chromogenic selection of the recombinant clones many vectors have been developed with positive selection capability allowing only the recombinant clones to grow in a selection medium. Most of these positive selection vectors have been developed based on insertional inactivation of lethal genes (Pierce et al., 1992, Proc. Natl. Acad. Sci. 89, 2056–2060; Henrich and Plapp, 1986, Gene 42, 345–349; Henrich and Schmidtberger, 1995, Gene 154, 51–54; Bernard et al., 1994, Gene 148, 71–74; Kuhn et al., 1986, Gene 42, 253–263; U.S. Pat. No. 5,910,438; U.S. Pat. No. 5,891,687). A vector system based on abolition of sensitivity towards metabolite has also been described (Kast, 1994, Gene 138,109–114). Vectors have also been constructed based on selection by means of DNA-degrading or RNA-degrading enzymes (Yazynin et al., 1996, Gene 169, 131–132; Ahrenhotz et al., 1994, Appl. Environ. Microbiol. 60, 3746–3751) as well as based on selection by destruction of long palindromic DNA sequences (Altenbuchner et al., 1992, Methods Enzymol. 216, 457–466).

The presently available positive selection vectors as well as other cloning vectors are associated with many disadvantages. An inherent problem of a vector with a lethal or a chromogenic gene is a high number of false positive clones, i.e., clones without any insert. The false positive clones could be revertants arising out of dominant mutations in the lethal or chromogenic gene rendering it inactive. However, the biggest disadvantage of every cloning system available today is the exonuclease-induced generation of false positive clones. The reagents used in restriction digestion, PCR and ligation, such as restriction enzymes, polymerases and ligases, are usually contaminated with exonucleases, which are seldom completely removed from larger lots of commercial preparations. Exonuclease digestion deletes some nucleotide bases from the cloning site in the chromogenic or lethal gene in a linearized vector DNA. Thus recircularization of such vectors results in inactivation of the chromogenic or lethal genes, and upon transformation, these recircularized vectors give false positive transformant clones. A palindromic sequence could also be destroyed by exonuclease digestion resulting in generation of false positive clones.

Insertion of a small DNA fragment in frame with the nucleotide sequence of the lethal gene or the chromogenic gene may in some cases not alter the function of the lethal or chromogenic gene, thus making it impossible to clone such small DNA fragments. Furthermore, when cloning of a small DNA fragment results in diminished function of the lethal gene, which nevertheless remains functional, then the recombinant clones grow at a reduced rate in case of positive selection vectors, and these clones could be confused with the non-recombinant clones growing because of diminished selection pressure due to, for example, long period of incubation.

A further disadvantage of the vectors based on lethal genes is that it may require a complex medium to activate the selection mechanism (Kast, 1994, Gene 138, 109–114). The positive selection vectors carrying lethal or chromogenic genes also require special host cells for transformation, e.g., CcdB based vectors require F⁻ host cells (U.S. Pat. No. 5,910,438), CAP based vectors require adenyl-cyclase positive host cells (U.S. Pat. No. 5,891,687) and lacZ based vectors require lac⁻ host cells (Messing et al., 1977, Proc. Natl. Acad. Sci. 79, 3642–3646; Norrander et al., 1983, Gene 26, 101–106; Yanisch-Perron et al., 1985, Gene 33, 103–119). A special regulatory system, usually lacI or CI repressor system (U.S. Pat. No. 5,910,438; Pierce et al., 1992, Proc. Natl. Acad. Sci. 89, 2056–2060), has also to be in place to prevent the expression of the lethal gene in the host cell during the preparation of vector DNA.

OBJECTS OF THE INVENTION

The primary object of the present invention is to develop a simple cloning and/or sequencing vector having the capability of positive selection thus allowing only the recombinant clones (carrying an insert DNA) to grow in a selection medium, whereas, the non-recombinant clones (carrying no insert DNA) would not grow. The vector could also be used as a positive selection expression vector.

The particular object of the present invention is to eliminate or greatly reduce the generation of false positive clones associated with all the presently available cloning systems. Especial emphasis is given to the elimination of exonuclease-induced false positive clones. Thus the present invention aims to apply the principle of insertional reconstruction of a reporter gene or a regulatory gene controlling the expression of a reporter gene. It was aimed to develop a positive selection vector based on insertional reconstruction of an antibiotic resistance reporter gene, which carries a dominant negative mutation at its 5' or 3' end. Thus upon transformation non-recombinant clones will not grow in presence of the respective antibiotic. Insertional reconstruction allows correction of the mutation in the antibiotic resistance reporter gene. Thus upon transformation of a host cell the reconstructed reporter gene produces functionally active antibiotic resistance reporter gene protein thus allowing the host cell to grow in a specific selection medium containing the respective antibiotic.

Use of the principle of reconstruction of a reporter gene should also greatly reduce, if not eliminate, revertants because firstly, probability of spontaneous mutational reconstruction of the wild-type reporter or regulatory gene is minimal, and secondly, any mutation in the coding sequence of the reporter or regulatory gene would rather negatively affect the function of the respective gene protein.

A vector system based on antibiotic resistance gene as the reporter gene should also eliminate the need of any special type of host cells.

The elimination of the disadvantages associated with the presently available vectors is greatly desirable. A vector system based on reporter gene reconstruction will mostly eliminate these disadvantages and hence will be a substantial technological achievement.

SUMMARY OF THE INVENTION

The present invention relates to a strategy for developing positive selection vectors based on reconstruction of a reporter gene or of a regulatory gene controlling the expression of a reporter gene. The invention also describes the use of such vectors for direct cloning of PCR products. As an example of application of the strategy, a positive selection vector pRGR1Ap has been developed. When the last (position 286) amino acid tryptophan (encoded by 5'-TGG-3') of ampicillin resistance gene β-lactamase is replaced by valine (encoded by 5'-GTG-3') β-lactamase becomes functionally inactive. The sequence 5'-GTG-3' is a part of the PmlI restriction endonuclease cleavage site 5'-CACGTG-3', which is a unique cloning site in this vector. Thus upon PmlI restriction endonuclease cleavage 5'-CAC-3' and 5'-GTG-3' are created at the 3' and 5' ends respectively of the linearized vector. A PCR primer carrying the nucleotides 5'-TGGTAA-3' at its 5' end is used in PCR. When the resulting blunt-ended PCR products thus obtained are ligated to the vector the reporter ampicillin resistance gene is reconstructed correcting the mutation. The nucleotides 5'-TAA-3' constitute the stop codon for the β-lactamase gene. Subsequent transformation of a host cell with the recombinant vector (carrying an insert DNA) produces functionally active β-lactamase, which confers resistance to ampicillin.

Restriction sites of ClaI, EcoRV, NarI, NdeI, NotI and SfiI have been introduced in this vector for easy extraction of the insert. The NarI site in the β-lactamase gene does not change the amino acid sequence of β-lactamase. Introduction of EcoRV restriction site in β-lactamase gene (bla) changes glutamic acid at position 277 into aspartic acid, whereas, the restriction site NdeI changes isoleucine into methionine at position 275, and glutamine into histidine at position 274. The restriction site ClaI in β-lactamase gene (bla) replaces methionine at position 268 with isoleucine. The mutations introduced by restriction sites NarI, EcoRV, NdeI and ClaI do not have any significant effect on the function of β-lactamase. Another vector pRGR2Ap, which is similar to pRGR1Ap, has been described. The vector pRGR2Ap contains pUC origin of replication, M13 origin of replication and T7 phage promoter.

BRIEF DESCRIPTION OF FIGURES

FIG. 2 shows the nucleotide sequence around the cloning site PmlI in pRGR1Ap (SEQ ID NO:1). An asterisk indicates a position of mutation in the ampicillin resistance gene.

FIG. 6 shows the nucleotide sequence around the cloning site PmlI in pRGR2Ap (SEQ ID NO:2).

DETAILED DESCRIPTION OF THE INVENTION

Figure 1:
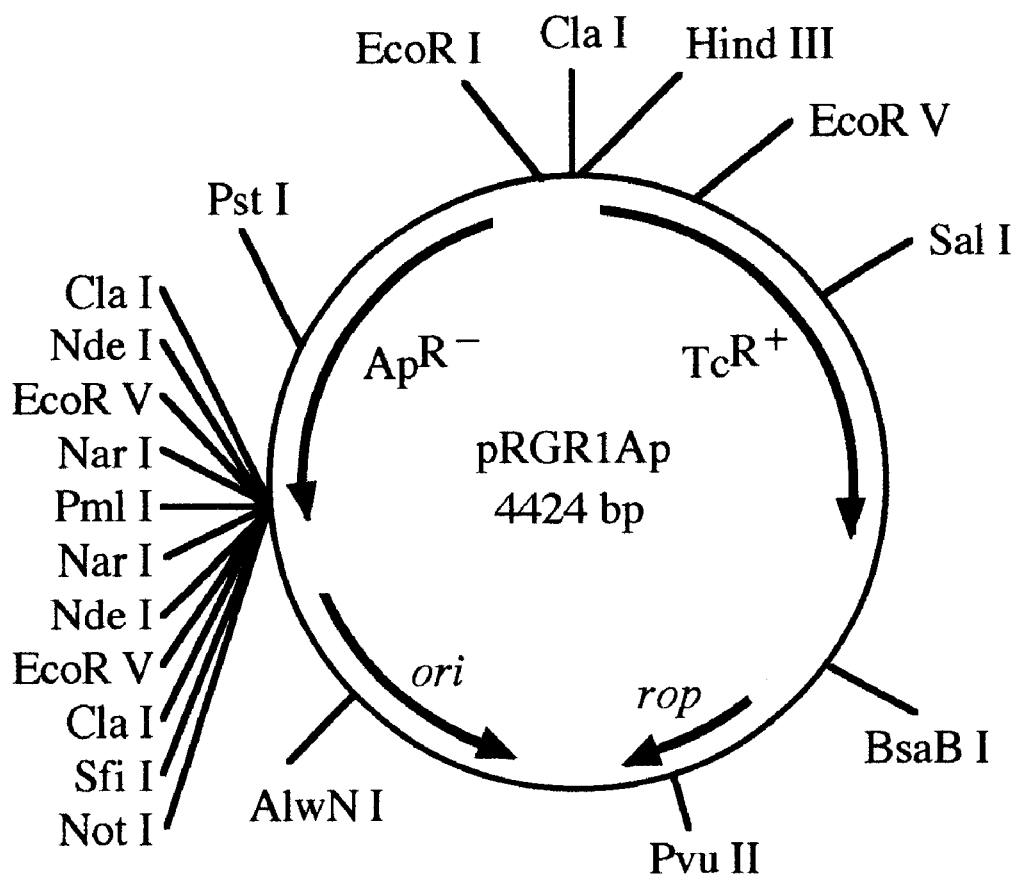
FIG. 1 shows an exemplary positive selection vector pRGR1Ap constructed according to the principle of reporter gene reconstruction. The ampicillin resistance gene is inactive due to a dominant negative mutation at its 3' end.

The present invention is directed to construct a positive selection vector system based on reconstruction of a reporter gene or a regulatory gene controlling the expression of a reporter gene. The invention also describes the use of such a vector for direct cloning of PCR generated DNA fragments. The vector carries a viral or plasmid origin for autonomous replication in an appropriate host cell. The vector contains an M13 or f1 origin of replication for easy isolation of single-stranded form of plasmid DNA upon coinfection of the host cells with a helper phage. It also carries a selectable marker gene, a reporter and/or regulatory gene with a dominant negative mutation, and a cloning site for inserting a PCR amplified DNA fragment or a restriction DNA fragment.

The invention envisions development of chromogenic or fluorogenic selection vectors based on reconstruction of the of lacZ or fluorescent protein genes. The invention also contemplates insertional reconstruction of a regulatory gene controlling the expression of lacZ or a fluorescent protein gene.

The selectable marker gene, which allows contamination-free growth of the host cells harboring the vector, is usually an antibiotic resistance gene, however, it could be an essential gene for the host or the vector itself. A chromogenic gene, such as lacZ or a fluorogenic gene, such as GFP (Green Fluorescent Protein) gene can also serve as a selectable marker gene.

The vector carries a reporter gene, the function of which could easily be assayed either qualitatively or quantitatively. Like the selectable marker gene, the reporter gene could be an antibiotic resistance gene, a toxic gene, an essential gene for the host or the vector, and a chromogenic gene, such as lacZ or a fluorogenic gene, such as a fluorescent protein gene.

When a positive selection vector is constructed based on insertional reconstruction of a reporter gene, the reporter gene is mutated in this vector so that upon transformation of a host cell the vector is unable to produce any functionally active reporter gene protein thus rendering the host cell unable to grow in a specific medium. When the positive selection vector is constructed based on insertional reconstruction of a regulatory gene, the reporter gene in this vector is functional, whereas, the regulatory gene carries the dominant negative mutation. Insertional reconstruction of the regulatory gene allows the host cell carrying the recombinant plasmid (containing an insert) to grow in a specific medium.

When the reporter gene is an antibiotic resistance gene and the vector is developed based on reconstruction of the reporter gene, the vector cannot produce the antibiotic resistance reporter gene protein resulting in inhibition of the growth of host cell in a specific selection medium containing the respective antibiotic. Only insertional reconstruction of the reporter gene will ensure production of the antibiotic resistance reporter gene protein thus allowing a host cell harboring the recombinant vector (carrying an insert DNA) to grow in a selection media containing the respective antibiotic.

A positive selection vector can be developed based on insertional reconstruction of a regulatory gene controlling the expression of a reporter gene. A vector can carry a reporter gene under the control of a positively regulated promoter, for example the cysD promoter (Malo and Loughlin, 1990, Gene 87, 127–131), or under the control of a negatively regulated promoter, for example, the lac promoter. The cysD promoter in $E.$ $coli$ is positively regulated by the positive regulatory (activator) CysB protein, which means binding of CysB protein to the cysD promoter initiates transcription from the cysD promoter. The lac promoter for lacZYA operon in $E.$ $coli$ is negatively controlled by the negative regulatory (repressor) LacI protein, which means binding of the LacI protein to the lac operator stops transcription from the lac promoter. Different combinations of regulatory genes and reporter genes could be used to develop multiple positive selection vectors. A positive selection vector could be developed carrying an antibiotic resistance reporter gene under the control of cysD promoter, and the cysB gene as the regulatory gene, wherein the cysB gene carries a dominant negative mutation. Only insertional reconstruction of the cysB gene will allow production of the antibiotic resistance reporter gene protein resulting in growth of only a host cell harboring a recombinant (carrying an insert DNA) clone in presence of the respective antibiotic. Similarly, a positive selection vector could be developed carrying a toxic reporter gene, e.g., ccdB gene, under the control of lac promoter, and the lacI gene as the regulatory gene, wherein the lacI gene carries a dominant negative mutation. Only insertional reconstruction of the lacI gene will inhibit production of the toxic gene protein resulting in growth of only a host cell harboring a recombinant (carrying an insert DNA) clone in a specific medium.

Chromogenic or fluorogenic selection vectors can be developed based on reconstruction of the reporter gene lacZ or fluorescent protein genes (e.g., GFP). LacZ or fluorescent protein genes under the control of a positive or a negative regulatory gene could also be used to develop chromogenic or fluorogenic selection vectors.

Positive selection vectors pRGR1Ap and pRGR2Ap have been developed based on insertional reconstruction of an antibiotic resistance reporter gene. These vectors carry a dominant mutation at the 3' end of the ampicillin resistance gene (bla) and the vectors carry an unique cloning site PmlI. When a PCR fragment carrying 5'-TGGTAA-3' at its 5' end is inserted into the PmlI digested vector then the ampicillin resistance gene is reconstructed. Subsequent transformation of a host cell with a recombinant vector results in production of ampicillin resistance gene protein β-lactamase and thus the transformant grows in presence of ampicillin. The vectors have been successfully used to clone PCR fragments amplified by Pfu or Taq DNA polymerase.

EXAMPLE 1

General Techniques of Molecular Biology

Unless otherwise indicated, the molecular biology techniques related to this invention are described in Sambrook et al., Molecular Cloning: A Laboratory Manual, Cold Spring Harbor Laboratory, Cold Spring Harbor, N.Y., 1989.

For enzymatic amplification of a targeted DNA fragment PCR was performed (Saiki et al., 1985, Science 230, 1350–1354; Mullis and Faloona, 1987, Method Enzymol. 155, 335–350) using a DNA thermal cycler (Perkin Elmer Cetus, Foster City, Calif., USA) according to the manufacturers instructions. The thermostable DNA polymerases and the PCR kit (Perkin Elmer Cetus, Foster City, Calif., USA; Stratagene, La Jolla, Calif., USA) were used according to the recommendations of the respective suppliers.

DNA restriction digestion was performed according o the specifications of the manufacturers (New England Biolabs, Beverly, Mass., USA; Stratagene, La Jolla, Calif., USA). After restriction digestion the restriction endonuclease was inactivated by heat treatment or by phenol:chloroform:isoamyl alcohol (25:24:1) treatment followed by ethanol precipitation of DNA. The precipitated DNA was then pelleted by centrifugation and the pellet was dried in air.

DNA ligation was achieved by incubating the DNA (vector and/or insert) in presence of T4 DNA ligase according to the instructions of the manufacturer (Life Technologies/GIBCO-BRL, Rockville, Md., USA).

Transformations of the commercially available competent host cells were carried out as per the instructions of the supplier (Life Technologies/GIBCO-BRL, Rockville, Md., USA). The transformants were plated onto LB agar medium (Life Technologies/GIBCO-BRL, Rockville, Md., USA) containing ampicillin (100 µg/ml, Sigma, St. Louis, Mo., USA) and/or tetracycline (12.5 µg(ml, Sigma, St. Louis, Mo., USA). For small or large scale preparation of transformant plasmid DNA, cells were grown on LB broth (Life Technologies/GIBCO-BRL, Rockville, Md., USA) containing ampicillin (100 µg/ml) and/or tetracycline (12.5 µg/ml) and DNA was prepared using alkaline lysis method.

The plasmids pUC19 (Norrander et al., 1983, Gene 26, 101–106) and pBR322 (Bolivar et al., 1977, Gene 2, 95–113) DNA were purchased from New England Biolabs (Beverly, Mass., USA) and $E.$ $coli$ DNA was obtained from Sigma (St. Louis, Mo., USA). Restriction endonucleases were purchased from New England Biolabs (Beverly, Mass., USA) and Stratagene (La Jolla, Calif., USA). Taq DNA polymerase and dNTPs were purchased from Perkin Elmer Cetus (Foster City, Calif., USA), and T4 DNA ligase was obtained from Life Technologies/GIBCO-BRL (Rockville, Md., USA). Pfu and Taqplus DNA polymerases were obtained from Stratagene (La Jolla, Calif., USA). Oligonucleotides were synthesized by Biosource International (Camarillo, Calif., USA). Kit for plasmid DNA extraction from agarose gel was purchased from Qiagen (Valencia, Calif., USA).

Construction of the Positive Selection Vector pRGR1Ap

It was aimed to generate a dominant negative mutant of the ampicillin resistance gene β-lactamase (bla) as well as to create restriction endonuclease cleavage sites in its 3' coding region. It was decided to introduce the restriction sites in β-lactamase by PCR-mediated mutagenesis, followed by testing the effect of each mutation.

The following forward PCR primer RGR1F was synthesized to introduce PmlI, NarI, EcoRV, NdeI and ClaI sites in the 3' coding region of β-lactamase. Introduction of the unique PmlI restriction site (5'-CACGTG-3') replaces the last amino acid (tryptophan at position 286, encoded by 5'-TGG-3') of β-lactamase with a valine (encoded by 5'-GTG-3'). The NarI site in the β-lactamase gene does not change the ammo acid sequence of β-lactamase. Introduction of EcoRV restriction site in β-lactamase gene changes glutamic acid in position 277 into aspartic acid, whereas, the restriction site NdeI changes isoleucine into methionine in position 275, and glutamine into histidine in position 274. The restriction site ClaI in β-lactamase gene (bla) replaces methionine in position 268 with isoleucine.

The following reverse PCR primer RGR1R was synthesized to introduce restriction sites of ClaI, EcoRV, NarI, NdeI, NotI and SfiI for easy extraction of the insert. Repeats of stop codons in all three reading frames were also introduced downstream of the β-lactamase gene. These stop codons would ensure that translation will be prematurely terminated in a recircularized non-recombinant vector, which would have been subjected to some exonuclease digestion. Thus the reporter gene protein will remain functionally inactive in a recircularized non-recombinant vector and minimize exonuclease-induced false positive clones.

Forward primer RGR1F:

5'-CAA TTA CAC GTG CTT AAT CAG TGA GGC GCC GAT ATC AGC CAT ATG TCT ATT TCG TTC ATC GAT AGT TGC CTG-3' (SEQ ID NO:3) (96 bases)

Reverse primer RGR1R:

5'-ATT AAG CAC GTG TAA TTG AAT AAT AGT TGA ATA GTA ATT GAA TAA GGC GCC ATA TGA TAT CGA TGG CCT AAG CGG CCG CTG TCA GAC CAA GTT TAC TCA TAT ATA CTT TAG-3' (SEQ ID NO:4) (111 bases)

The PCR conditions were:

1 ng pBR322 DNA

10 $\mu$M forward primer RGR1F

10 $\mu$M reverse primer RGR1R 0.2 mM dNTPs (equimolar mixture of dATP, dGTP, dCTP and dTTP)

2.5 $\mu$l of 10×low salt buffer for Taqplus DNA polymerase.

2.5 U Taqplus DNA polymerase (Stratagene, La Jolla, Calif., USA)

Distilled water making total volume up to 25 $\mu$l.

Two drops of mineral oil was added to overlay on the PCR mixture to prevent evaporation during PCR cycling.

The PCR cycle conditions were as follows:

2 min at 94° C., then 15 cycles with: 1 min at 94° C., 1 min at 55° C., 8 min at 72° C.; followed by a final extension step of 10 min at 72° C.

To verify the PCR reaction, 5 $\mu$l of the PCR product was electrophoresed in 0.8% agarose (Life Technologies/GIBCO-BRL, Rockville, Md., USA) gel in presence of ethidium bromide (Sigma, St. Louis, Mo., USA) for about 1 hr, and the gel was then photographed under UV light using Polaroid Type 667 films (Fisher Scientific, Suwanee, Ga., USA). The rest of the PCR amplified DNA was treated with phenol:chloroform:isoamyl alcohol (25:24:1) and was then precipitated by ethanol. Precipitated DNA was pelleted by centrifugation and the pellet was dried in air. The dried DNA was dissolved in 25 $\mu$l of 1×PmlI restriction buffer and then incubated in presence of 20 U of PmlI restriction endonuclease for 1 hr at 37° C. The digested DNA was electrophoresed in 0.8% agarose gel. The desired DNA band was excised and DNA was purified using Qiaex kit. The purified DNA was used in ligation as per conditions given below:

15 $\mu$l of purified DNA

4 $\mu$l of 5×ligation buffer

1 $\mu$l (5 U) of T4 DNA ligase (Life Technologies/GIBCO-BRL, Rockville, Md., USA)

Ligation was performed for overnight at 16° C.

An aliquot of 2 $\mu$l ligation mix was used to transform 50 $\mu$l Maxefficiency DH5α (Life Technologies/GIBCO-BRL, Rockville, Md., USA) E. coli host cells according to the recommended protocols. The transformants were then plated onto LB agar plates containing 12.5 $\mu$g/ml tetracycline and incubated at 37° C. overnight. Some transformant colonies were individually transferred to LB agar plates containing 100 $\mu$g/ml ampicillin as well as to LB agar plates containing 12.5 $\mu$g/ml tetracycline. The clones sensitive to ampicillin were then individually grown in 5 ml aliquot of LB broth containing 12.5 $\mu$g/ml tetracycline. Small scale plasmid DNA was isolated from each individual clone, and DNA was then digested with 20 U PmlI restriction endonuclease. Any plasmid DNA carrying a PmlI cleavage site was further characterized for the presence of other expected restriction endonuclease cleavage sites. One such plasmid carrying expected restriction endonuclease cleavage sites was named as pRGR1Ap and the restriction map of this vector is shown in FIG. 1. The vector pRGR1Ap is sensitive to ampicillin, and hence carries a dominant negative mutation in the 3' coding region of β-lactamase because of mutations introduced by the restriction sites. FIG. 2 shows the DNA sequence indicating the positions of mutations in β-lactamase gene in pRGR1Ap, and also the mutated and other related restriction sites.

To test the effect of $^{Trp}286_{Val}$ mutation (created by PmlI) it was decided to clone a PCR fragment carrying 5'-TGGTAA-3' at its 5' end into the PmlI digested pRGR1Ap resulting in correction of the mutation. Large scale DNA of pRGR1Ap was prepared using plasmid kit from Qiagen. An aliquot of 2 $\mu$g of pRGR1Ap DNA was digested with 20 U of PmlI restriction endonuclease for 1 hr at 37° C. The digest was then incubated at 70° C. for 30 min to inactivate PmlI, and was diluted with sterile DEPC-treated water to give final concentration 10 ng/$\mu$l. The vector pRGR1Ap thus prepared was tested for direct cloning of PCR products as well as for its capability as a positive selection vector.

Example of Direct Cloning of PCR Product Into pRGR1Ap

A 420 bp fragment of the lacZ was separately PCR-amplified using Taq DNA polymerase (without 3'-5' proof reading exonuclease activity) and Pfu DNA polymerase (with 3'-5' proof reading exonuclease activity).

Following are the primers used in amplification of the above mentioned 420 bp DNA fragment:

Forward primer LC1261RGRF:

5'-TGG TAA GCT TGC GGC CGC AAA GGC CAC AAT TTC ACA CAG GAA ACA GCT ATG-3' (SEQ ID NO:5) (51 bases)

Reverse primer LC1680R:

5'-TTT CAT CAA CAT TAA ATG TGA GCG AGT AAC-3' (SEQ ID NO:6) (30 bases)

The forward primers LC1261RGRF carries 5'-TGGTAA-3' at its 5' end and NotI and SfiI sites for elucidation of the orientation of the insert in a recombinant plasmid.

The PCR conditions were:

1 μg E. coli DNA

10 μM forward primer (LC1261RGRF)

10 μM reverse primer (LC1680R)

0.2 mM dNTPs (equimolar mixture of dATP, dGTP, dCTP and dTTP)

2.5 μl of 10×buffer for Taq or Pfu DNA polymerase 2.5 U Taq or Pfu DNA polymerase Distilled water making total volume up to 25 μl.

Two drops of mineral oil was added to overlay on the PCR mixture to prevent evaporation during PCR cycling.

The PCR cycle conditions were as follows:

2 min at 94° C., then 25 cycles with: 1 min at 94° C., 1 min at 55° C., 2 min at 72° C.; followed by a final extension step of 5 min at 72° C.

To verify the PCR reaction, 5 μl of the PCR product was electrophoresed in 1.5% agarose gel in presence of ethidium bromide for about 1 hr, and the gel was then photographed under UV light using Polaroid Type 667 films.

Ligation was performed using 1–200 ng of PmlI digested pRGR1Ap vector DNA, and 1–5 μl of the PCR product. The conditions of a typical ligation experiment is given below:

1 μl (50 ng) of PmlI digested vector pRGR1Ap DNA

2 μl (200 ng) of PCR product

4 μl of 5×ligase buffer

12 μl of DEPC-treated water

1 μl (5 U) of T4 DNA ligase

Ligation mixture was incubated at room temperature for 5–30 min or at 16° C. for overnight.

Different amounts (2–10 μl) of ligation mix were used to transform 10–100 μl of competent Maxefficiency DH5α E. coli cells (Life Technologies/GIBCO-BRL, Rockville, Md., USA). In a typical transformation 50 μl of DH5α was transformed with 2 μl of ligation mixture for 30 min on ice, followed by heat shock at 42° C. for 50 sec, 2 min on ice, addition of 1.0 ml of SOC medium (Life Technologies/GIBCO-BRL, Rockville, Md., USA), and incubation at 37° C. for 1 hr. An aliquot of 25–500 μl of the transformation mix was plated onto LB agar plates containing 100 μg/ml ampicillin and 12.5 μg/ml tetracycline and incubated overnight at 37° C. As expected, control ligation sample of vector alone gave only a few transformant, whereas, ligation samples of vector plus PCR fragments gave many transformant colonies. The result of this typical cloning experiment is shown in Table 1. Some transformant clones were individually cultured in 5 ml LB broth containing 100 μg/ml ampicillin and 12.5 μg/ml tetracycline for overnight at 37° C. Small scale plasmid DNA was isolated using standard alkaline lysis method (Sambrook et al., Molecular Cloning: A Laboratory Manual, Cold Spring Harbor Laboratory, Cold Spring Harbor, N.Y., 1989). The isolated plasmid DNA was characterized by NotI or SfiI restriction endonuclease digestion, which should release the insert fragment.

TABLE 1

| pRGR1Ap[a] (vector used in ligation) | PCR fragment (polymerase used) | colonies/ml transformation mix[b] | positive clones/ analyzed clones[c] |
|---|---|---|---|
| 50 ng | 2 μl (Taq DNA polymerase) | 396 | 9/9 |
| 50 ng | 2 μl (Pfu DNA polymerase) | 1120 | 9/9 |
| 50 ng | — | 4 | — |

[a]The positive selection vector pRGR1Ap was digested with Pml I restriction enzyme, and after heat inactivation of Pml I the vector DNA was used in ligation.
[b]Transformants were grown in presence of 100 μg/ml ampicillin and 12.5 μg/ml tetracycline.
[c]The plasmids from the transformants were digested with either Not I or Sfi I releasing the insert.

As expected, Table 1 shows that the vector pRGR1Ap is capable of cloning the PCR fragments carrying 5'-TGGTAA-3' at its 5' end as produced by primers LC1261RGRF and LC1680R. Table 1 also shows that the vector pRGR1Ap is capable of cloning both types of PCR products produced by Taq and Pfu DNA polymerases. However, fewer number of clones are obtained in case of cloning of the PCR products obtained by Taq DNA polymerase because in such case only those PCR products of Taq DNA polymerase are ligated which have no dAMP overhang. Improved efficiency of cloning of the PCR products generated with Taq DNA polymerase could be achieved by treating the PCR products with a DNA polymerase with 3'-5' proof-reading exonuclease activity (T4 DNA polymerase, Pfu DNA polymerase etc.) thus removing the overhang dAMP (Costa and Weiner, 1994, Nucl. Acids Res. 22, 2423). The result also shows that 100% of the analyzed clones carried the 420 bp insert, which confirms the positive selection capability of the vector pRGR1Ap. The results also indicate that the other mutations have minimum effect on the function of β-lactamase, and hence PmlI could be used as the unique cloning site. The DNA sequence and restriction sites around the cloning site PmlI is also shown in FIG. 2.

Use of pRGR1Ap Eliminates Exonuclease-induced False Positive Clones

A positive selection vector developed based on reconstruction of a reporter gene should greatly reduce, if not eliminate, generation of false positive clones. Thus pRGR1Ap was tested for its capability of eliminating false positive clones in a cloning experiment. An aliquot of 1 μg of the vector pRGR1Ap was digested with 20 U of PmlI for 1 hr and another aliquot of 1 μg of the vector pRGR1Ap was digested with 100 U of PmlI for 4 hr at 37° C. Similarly, an aliquot of 1 μg of the vector pUC19 was digested with 20 U of SmaI for 1 hr and another aliquot of 1 μg of the vector pUC19 was digested with 100 U of SmaI for 4 hr at 25° C. The digests were treated at 70° C. for 30 min to inactivate the restriction endonucleases. The digested vectors were then diluted with water (10 ng/μl) and recircularized by ligation, the conditions of which are given below:

1 μl (10 ng) of vector DNA

4 μl of 5×ligase buffer

14 μl of DEPC-treated water

1 μl of T4 DNA ligase

Ligation mixture was incubated at 16° C. for overnight.

An aliquot of 2 μl of ligation mix was used to transform 50 μl of competent Maxefficiency DH5α E. coli cells for 30 min on ice, followed by heat shock at 42° C. for 50 sec, 2 min on ice, addition of 1.0 ml of SOC medium, and incubation at 37° C. for 1 hr. For the pUC19 derivatives, an aliquot of 50 μl of the transformation mix was plated onto LB agar plates containing 100 μg/ml ampicillin, 100 ng/ml X-gal and 1 mM IPTG and incubated overnight at 37° C. For the pRGR1Ap derivatives, cells from 1 ml transformation mix were spun down, resuspended in 50 μl of S.O.C. medium, and was then plated onto LB agar plates containing 100 μg/ml ampicillin and 12.5 μg/ml tetracycline and incubated overnight at 37° C. In case of pUC19 derivatives, all white colonies were considered false positive clones, whereas, the blue colonies were wild-type clones. In case of pRGR1Ap derivatives all clones were considered false positive clones. Table 2 shows the effect of exonuclease digestion for generating false positive clones in a cloning experiment.

TABLE 2

| Vector used in ligation[a] | Amount of DNA (μg) | Enzyme (units) | Period of Incubation (h) | Colonies/ml transformation mix[b] | False positive clones[c] |
|---|---|---|---|---|---|
| pRGR1Ap | 1 | 20 | 1 | 4 | 4 |
| pRGR1Ap | 1 | 100 | 4 | 7 | 7 |
| pUC19 | 1 | 20 | 1 | 90,000 | 4,400 |
| pUC19 | 1 | 100 | 4 | 36,000 | 17,000 |

[a]The positive selection vector pRGR1Ap and the chromogenic selection vector pUC19 were separately digested with Pml I and Sma I respectively, and after heat inactivation of restriction enzymes each digest (10 ng) was subjected to self-ligation.
[b]For pRGR1Ap derivatives, transformants were grown in presence of 100 μg/ml ampicillin and 12.5 μg/ml tetracycline, whereas, for pUC19 derivatives, transformants were grown in presence of 100 μg/ml ampicillin.
[c]In case of pRGR1Ap derivatives, all colonies were considered false positive clones. In case of pUC19 derivatives, all white colonies were considered false positive clones, whereas, the blue colonies were considered wild-type clones.

It is evident form the data in Table 2 that contaminating exonuclease greatly increases the number of false positive clones in case of pUC19, wherein the cloning site in pUC19 is in the chromogenic lacZ gene. This result also shows that exonuclease has very little effect on generating false positive clones in case of pRGR1Ap. The possibility of these false positive clones arising from spontaneous mutations were considered unlikely, because in such case the number of false positive clones should have been similar in case of both vectors.

EXAMPLE 2

Construction of pBR322Δrop1

It was decided to construct a positive selection vector with multiple added features. The vector should contain a pUC origin of replication thus giving higher copy number in *E. coli* compared to pRGR1Ap, which is a derivative of pBR322. The vector also should contain an M13 or f1 origin of replication to generate single-stranded form of DNA after co-infection with a helper phage phage. Furthermore, the vector should carry a phage promoter around the cloning site for easy in vitro production of RNA probes of the insert DNA.

The rop gene in pBR322 is responsible for inhibition of copy number and deletion of rop is responsible for higher copy number of pUC vectors in *E. coli*. Thus it was decided to delete the rop gene from pBR322 using PCR-mediated mutagenesis. The following forward PCR primer PUC681F and reverse primer PBR1380R were synthesized. The PCR product generated from pBR322 using these two primers would not contain the rop gene.

Forward primer PUC681F:
5'-GTC GCA AGA TCT TGA AAG CTT GCG CTC TTC CGC TTC CTC GCT CAC-3' (SEQ ID NO:7) (45 bases)
Reverse primer PBR1380R:
5'-CTG AGC AGA TCT TAA TCT AGA GTT CTG CCA AGG GTT GGT TTG CGC-3' (SEQ ID NO:8) (45 bases)

The forward primer PUC681F carries the restriction sites BglII and HindIII at its 5' end. The reverse primer PBR1380R also carries BglII and XbaI restriction sites at its 5' end.

Recircularization of the PCR product after BglII digestion would give the desired plasmid.

The PCR conditions were:
1 ng pBR322 DNA
10 μM forward primer PUC681F
10 μM reverse primer PBR1380R
0.2 mM dNTPs (equimolar mixture of dATP, dGTP, dCTP and dTTP)
2.5 μl of 10×low salt buffer for Taqplus DNA polymerase.
2.5 U Taqplus DNA polymerase
Distilled water making total volume up to 25 μl.
Two drops of mineral oil was added to overlay on the PCR mixture to prevent evaporation during PCR cycling.
The PCR cycle conditions were as follows:
2 min at 94° C., then 15 cycles with: 1 min at 94° C., 1 min at 55° C., 8 min at 72° C.; followed by a final extension step of 10 min at 72° C.

To verify the PCR reaction, 5 μl of the PCR product was electrophoresed in 0.8% agarose gel in presence of ethidium bromide for about 1 hr, and the gel was then photographed under UV light using Polaroid Type 667 films. The rest of the PCR amplified DNA was treated with phenol:chloroform:isoamyl alcohol (25:24:1) and was then precipitated by ethanol. Precipitated DNA was pelleted by centrifugation and the pellet was dried in air. The dried DNA was dissolved in 25 μl of 1×BglII restriction buffer and then incubated in presence of 20 U of BglII restriction endonuclease for 1 hr at 37° C. The digested DNA was electrophoresed in 0.8% agarose gel. The desired DNA band was excised and DNA was purified using Qiaex kit. The purified DNA was used in ligation as per conditions given below:
15 μl of purified DNA
4 μl of 5×ligation buffer
1 μl (5 U) of T4 DNA ligase
Ligation was performed for overnight at 16° C.

Figure 3:
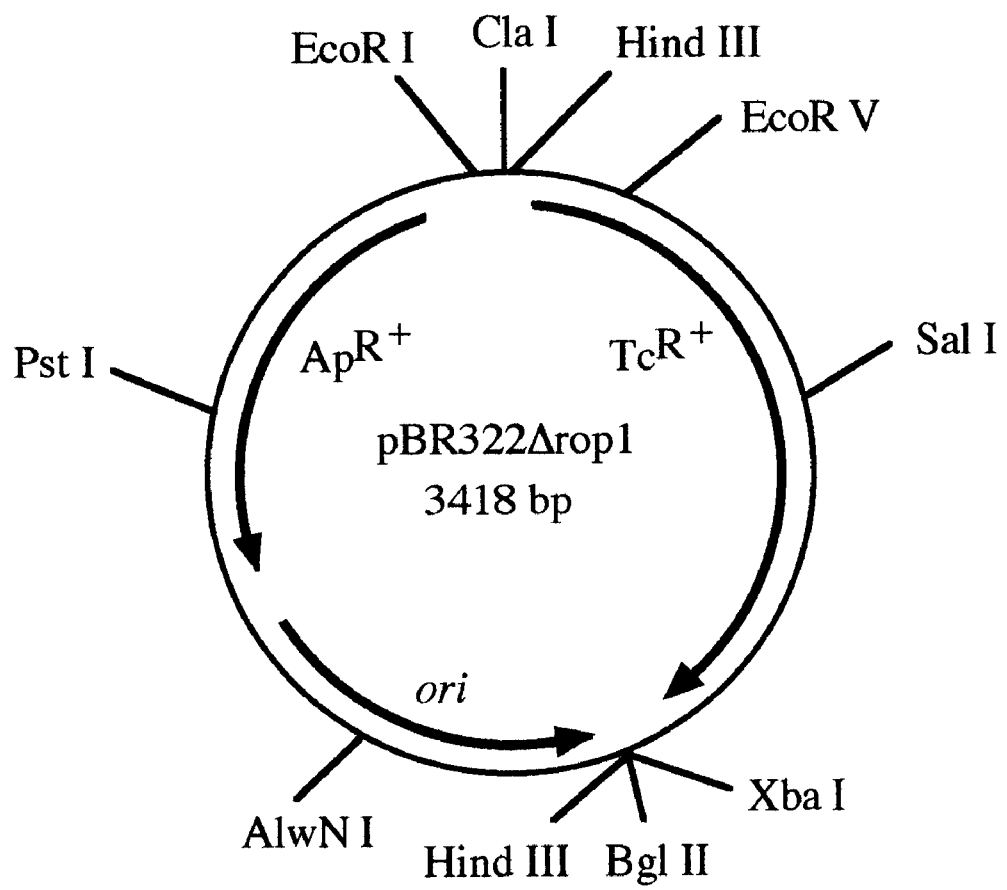
FIG. 3 shows the restriction map of pBR322Δrop1.

An aliquot of 2 μl ligation mix was used to transform 50 μl Maxefficiency DH5α *E. coli* host cells according to the recommended protocols. The transformants were then plated onto LB agar plates containing 100 μg/ml ampicillin and 12.5 μg/ml tetracycline and incubated at 37° C. overnight. Some transformant colonies were individually grown in 5 ml aliquot of LB broth containing 100 μg/ml ampicillin and 12.5 μg/ml tetracycline. Small scale plasmid DNA was isolated from each individual clone, and DNA was then digested with 20 U BglII restriction endonuclease. Any plasmid DNA carrying a BglII cleavage site was further characterized for the presence of other expected restriction endonuclease cleavage sites. One such plasmid carrying expected restriction endonuclease cleavage sites was named as pBR322Δrop1 and the restriction map of this vector is shown in FIG. 3. With respect to copy number in *E. coli* the plasmid pBR322Δrop1 is equivalent to the pUC vectors.

Construction of pBR322Δrop1M13.2

It was decided to add the M13 origin of replication to pBR322Δrop1 which would allow generation of single-stranded form of DNA after co-infection with wild-type M13 or f1 or another helper phage. The following forward PCR primer PUC119.500F and reverse primer PUC119.980R were synthesized to amplify the M13 origin region from pUC119.

Forward primer PUC119.500F:

5'-GGA AGA TCT AAG CTT ACG TCA AAG CAA CCA TAG TAC GCG CCC-3' (SEQ ID NO:9) (42 bases)

Reverse primer PUC119.980R:

5'-GGA AGA TCT CCA TAA AAT TGT AAA CGT TAA TAT TTT GTT AAA ATT CGC-3' (SEQ ID NO:10) (48 bases)

The forward primer PUC119.500F carries the restriction sites BglII and HindIII at its 5' end. The reverse primer PUC119.980R also carries a BglII restriction site at its 5' end. Ligation of the BglII digested PCR product and pBR322Δrop1 would generate the desired plasmid.

The PCR conditions were:

1 ng pUC119 DNA

10 μM forward primer PUC119.500F

10 μM reverse primer PUC119.980R 0.2 mM dNTPs (equimolar mixture of dATP, dGTP, dCTP and dTTP)

2.5 μl of 10×low salt buffer for Taqplus DNA polymerase 2.5 U Taqplus DNA polymerase Distilled water making total volume up to 25 μl.

Two drops of mineral oil was added to overlay on the PCR mixture to prevent evaporation during PCR cycling.

The PCR cycle conditions were as follows:

2 min at 94° C., then 20 cycles with: 1 min at 94° C., 1 min at 55° C., 2 min at 72° C.; followed by a final extension step of 5 min at 72° C.

To verify the PCR reaction, 5 μl of the PCR product was electrophoresed in 1.5% agarose gel in presence of ethidium bromide for about 1 hr, and the gel was then photographed under UV light using Polaroid Type 667 films. The rest of the PCR amplified DNA was treated with phenol:chloroform:isoamyl alcohol (25:24:1) and was then precipitated by ethanol. Precipitated DNA was pelleted by centrifugation and the pellet was dried in air. The dried DNA was dissolved in 25 μl of 1×BglII restriction buffer and then incubated in presence of 20 U of BglII restriction endonuclease for 1 hr at 37° C. The digested DNA was electrophoresed in 1.5% agarose gel. The desired DNA band was excised and DNA was purified using Qiaex kit. The purified DNA was used in ligation. The plasmid pBR322Δrop1 was also digested with BglII and DNA was treated with phenol:chloroform:isoamyl alcohol (25:24:1) and was then precipitated by ethanol. Precipitated DNA was pelleted by centrifugation and the pellet was dried in air, dissolved in water and then used in ligation in conjunction with the purified PCR product. The conditions of ligation are given below:

10 μl of purified PCR DNA

5 μl of pBR322Δrop1 DNA

4 μl of 5×ligation buffer

1 μl (5 U) of T4 DNA ligase

Ligation was performed for overnight at 16° C.

Figure 4:
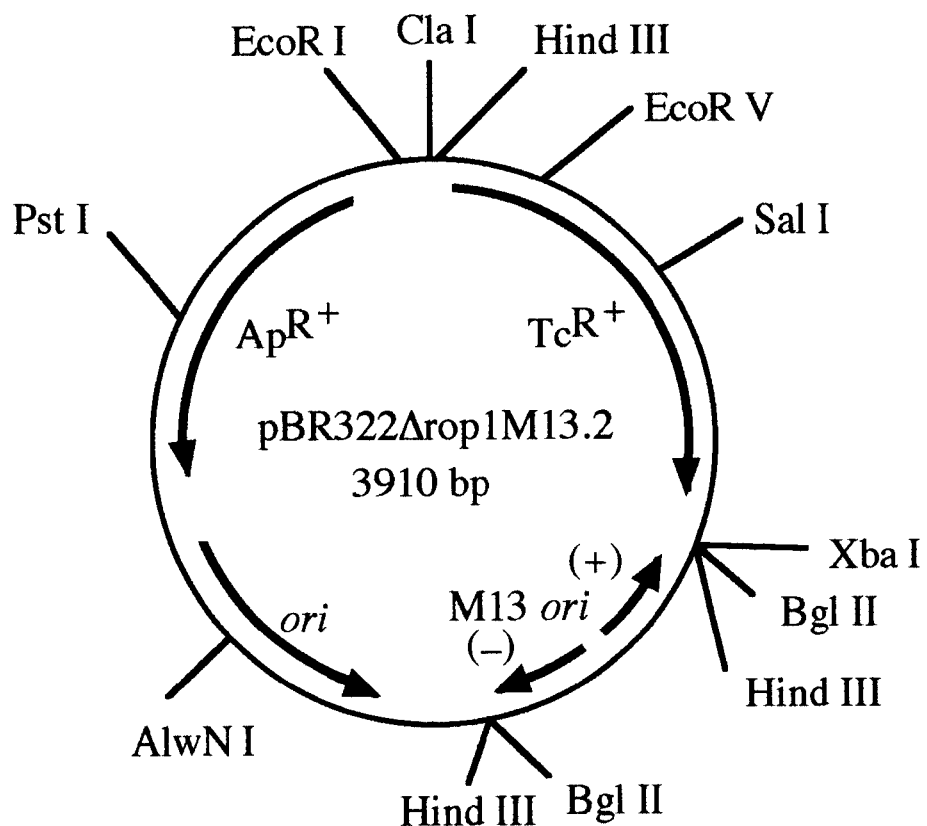
FIG. 4 shows the restriction map of pBR322Δrop1M13.2.

An aliquot of 2 μl ligation mix was used to transform 50 μl Maxefficiency DH5α E. coli host cells according to the recommended protocols. The transformants were then plated onto LB agar plates containing 100 μg/ml ampicillin and 12.5 μg/ml tetracycline and incubated at 37° C. overnight. Some transformant colonies were individually grown in 5 ml aliquot of LB broth containing 100 μg/ml ampicillin and 12.5 μg/ml tetracycline. Small scale plasmid DNA was isolated from each individual clone, and DNA was then digested with 20 U BglII restriction endonuclease. Any plasmid DNA carrying a 480 bp BglII fragment was further characterized for the presence of other expected restriction endonuclease cleavage sites. One such plasmid carrying expected restriction endonuclease cleavage sites was named as pBR322Δrop1M13.2 and the restriction map of this vector is shown in FIG. 4. When infected with M13mp18 the single-stranded form of pBR322Δrop1M13.2 was obtained.

Construction of the Positive Selection Vector pRGR2Ap

It was decided to develop a positive selection vector based on reporter gene reconstruction which would be a derivative of pBR322Δrop1M13.2 carrying the features of pRGR1Ap as well as would contain the T7 phage promoter sequence around the cloning site for easy in vitro production of RNA probes of the insert DNA.

The following forward PCR primer RGR1F was synthesized to introduce PmlI, NarI, EcoRV, NdeI and ClaI sites in the 3' coding region of β-lactamase. Introduction of the unique PmlI restriction site (5'-CACGTG-3') replaces the last (position 286) tryptophan (5'-TGG-3') of β-lactamase with a valine (5'-GTG-3'). The NarI site in the β-lactamase gene does not change the amino acid sequence of β-lactamase. Introduction of EcoRV restriction site in β-lactamase gene (bla) changes glutamic acid in position 277 into aspartic acid, whereas, the restriction site NdeI changes isoleucine into methionine in position 275, and glutamine into histidine in position 274. The restriction site ClaI in β-lactamase gene (bla) replaces methionine in position 268 with isoleucine.

Forward primer RGR1F:

5'-CAA TTA CAC GTG CTT AAT CAG TGA GGC GCC GAT ATC AGC CAT ATG TCT ATT TCG TTC ATC GAT AGT TGC CTG-3' (SEQ ID NO:3) (96 bases)

The following reverse PCR primer RGR2R was synthesized to introduce the T7 phage promoter and restriction sites of ClaI, EcoRV, NarI, NdeI, NotI and SfiI for easy extraction of the insert. Repeats of stop codons in all three reading frames were also introduced downstream of the β-lactamase gene. These stop codons would ensure that translation will be prematurely terminated in a recircularized non-recombinant vector, which would have been subjected to some exonuclease digestion. Thus the reporter gene protein will remain functionally inactive in a recircularized non-recombinant vector and minimize exonuclease-induced false positive clones.

Reverse primer RGR2R:

5'-ATT AAG CAC GTG TAA TTG AAT AAT AGT TGA ATA GTA ATT GAA TAA CTA TAG TGA GTC GTA TTA GGC GCC ATA TGA TAT CGA TGG CCA AAG CGG CCG CTG TCA GAC CAA GTT TAC TCA TAT ATA CTT TAG-3' (SEQ ID NO:11) (129 bases)

PCR product generated from pBR322Δrop1M13.2 using primers RGR1F and RGR2R would be digested with PmlI and subsequent recircularization would give the desired vector.

The PCR conditions were:

1 ng pBR322Δrop1M13.2 DNA

10 μM forward primer RGR1F

10 μM reverse primer RGR2R 0.2 mM dNTPs (equimolar mixture of dATP, dGTP, dCTP and dTTP)

2.5 μl of 10×low salt buffer for Taqplus DNA polymerase 2.5 U Taqplus DNA polymerase Distilled water making total volume up to 25 μl.

Two drops of mineral oil was added to overlay on the PCR mixture to prevent evaporation during PCR cycling.

The PCR cycle conditions were as follows:

2 min at 94° C., then 15 cycles with: 1 min at 94° C., 1 min at 55° C., 8 min at 72° C.; followed by a final extension step of 10 min at 72° C.

To verify the PCR reaction, 5 μl of the PCR product was electrophoresed in 0.8% agarose gel in presence of ethidium bromide for about 1 hr, and the gel was then photographed under UV light using Polaroid Type 667 films. The rest of the PCR amplified DNA was treated with phenol:chloroform:isoamyl alcohol (25:24:1) and was then precipitated by ethanol. Precipitated DNA was pelleted by centrifugation and the pellet was dried in air. The dried DNA was dissolved in 25 μl of 1×PmlI restriction buffer and then incubated in presence of 20 U of PmlI restriction endonuclease for 1 hr at 37° C. The digested DNA was electrophoresed in 0.8% agarose gel. The desired DNA band was excised and DNA was purified using Qiaex kit. The purified DNA was used in ligation as per conditions given below:

15 μl of purified DNA

4 μl of 5×ligation buffer

1 μl (5 U) of T4 DNA ligase

Ligation was performed for overnight at 16° C.

Figure 5:
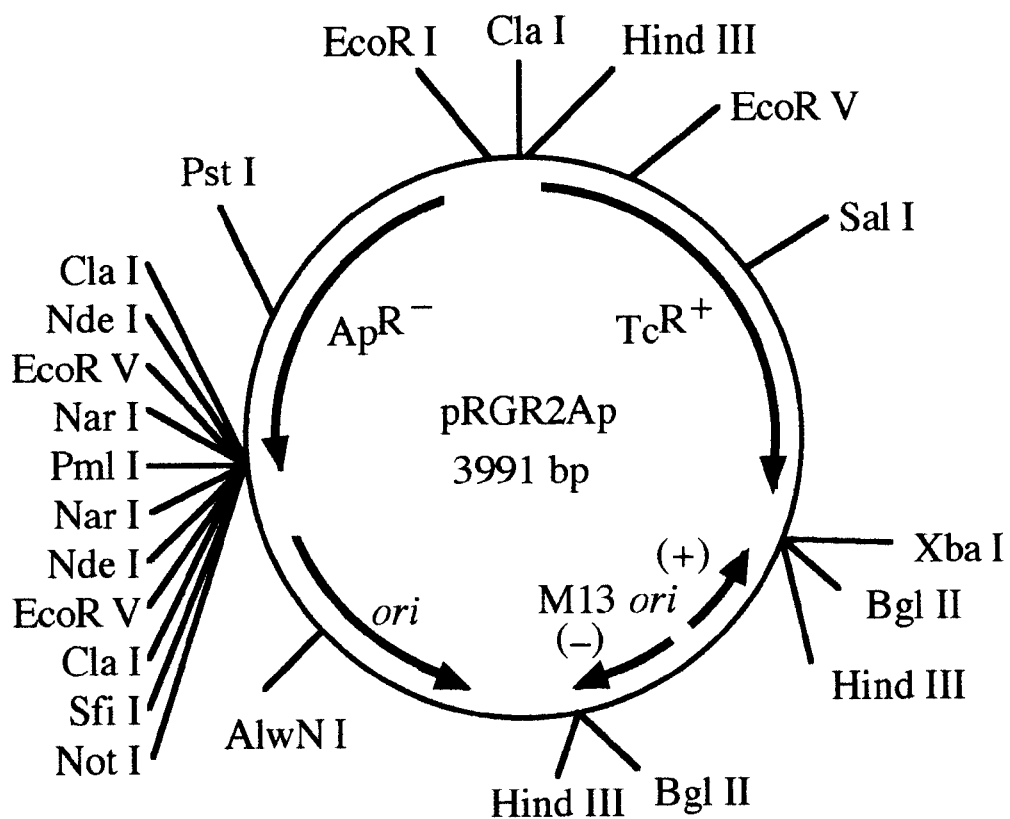
FIG. 5 shows the restriction map of pRGR2Ap. The ampicillin resistance gene is inactive due to a dominant negative mutation at its 3' end.

An aliquot of 2 μl ligation mix was used to transform 50 μl Maxefficiency DH5α E. coli host cells according to the recommended protocols. The transformants were then plated onto LB agar plates containing 12.5 μg/ml tetracycline and incubated at 37° C. overnight. Some transformant colonies were individually transferred to LB agar plates containing 100 μg/ml ampicillin as well as to LB agar plates containing 12.5 μg/ml tetracycline. The clones sensitive to ampicillin were then individually grown in 5 ml aliquot of LB broth containing 12.5 μg/ml tetracycline. Small scale plasmid DNA was isolated from each individual clone, and DNA was then digested with 20 U PmlI restriction endonuclease. Any plasmid DNA carrying a PmlI cleavage site was further characterized for the presence of other expected restriction endonuclease cleavage sites. One such plasmid carrying expected restriction endonuclease cleavage sites was named as pRGR2Ap and the restriction map of this vector is shown in FIG. 5. The vector pRGR2Ap is sensitive to ampicillin, and hence carries a dominant negative mutation in the 3' coding region of β-lactamase because of mutation introduced by the restriction sites. FIG. 6 shows the DNA sequence indicating the PmlI cloning site, T7 phage promoter sequence, and other related restriction sites in pRGR2Ap.

Example of Direct Cloning of PCR Product Into pRGR2Ap

A 420 bp fragment of the lacZ was separately PCR-amplified using Taq DNA polymerase (without 3'-5' proof reading exonuclease activity) and Pfu DNA polymerase (with 3'-5' proof reading exonuclease activity).

Following are the primers used in amplification of the above mentioned 420 bp DNA fragment:

Forward primer LC1261RGRF:

5'-TGG TAA GCT TGC GGC CGC AAA GGC CAC AAT TTC ACA CAG GAA ACA GCT ATG-3' (SEQ ID NO:5) (51 bases)

Reverse primer LC1680R:

5'-TTT CAT CAA CAT TAA ATG TGA GCG AGT AAC-3' (SEQ ID NO:6) (30 bases)

The PCR conditions were:

1 μg E. coli DNA

10 μM forward primer (LC1261RGRF)

10 μM reverse primer (LC1680R)

0.2 mM dNTPs (equimolar mixture of dATP, dGTP, dCTP and dTTP)

2.5 μl of 10×buffer for Taq or Pfu DNA polymerase 2.5 U Taq or Pfu DNA polymerase Distilled water making total volume up to 25 μl.

Two drops of mineral oil was added to overlay on the PCR mixture to prevent evaporation during PCR cycling.

The PCR cycle conditions were as follows:

2 min at 94° C., then 25 cycles with: 1 min at 94° C., 1 min at 55° C., 2 min at 72° C.; followed by a final extension step of 5 min at 72° C.

To verify the PCR reaction, 5 μl of the PCR product was electrophoresed in 1.5% agarose gel in presence of ethidium bromide for about 1 hr, and the gel was then photographed under UV light using Polaroid Type 667 films.

Ligation was performed using 1–200 ng of PmlI digested pRGR2Ap vector DNA, and 1–5 μl of the PCR product. The conditions of a typical ligation experiment is given below:

1 μl (50 ng) of PmlI digested vector pRGR2Ap DNA

2 μl (200 ng) of PCR product

4 μl of 5×ligase buffer

12 μl of DEPC-treated water

1 μl (5 U) of T4 DNA ligase

Ligation mixture was incubated at room temperature for 5–30 min or at 16° C. for overnight.

Different amounts (2–10 μl) of ligation mix were used to transform 10–100 μl of competent Maxefficiency DH5α E. coli cells. In a typical transformation 50 μl of DH5α was transformed with 2 μl of ligation mixture for 30 min on ice, followed by heat shock at 42° C. for 50 sec, 2 min on ice, addition of 1.0 ml of SOC medium, and incubation at 37° C. for 1 hr. An aliquot of 25–500 μl of the transformation mix was plated onto LB agar plates containing 100 μg/ml ampicillin and 12.5 μg/ml tetracycline and incubated overnight at 37° C. As expected, control ligation sample of vector alone gave only a few transformant, whereas, ligation samples of vector plus PCR fragments gave many transformant colonies. Some transformant clones were individually cultured in 5 ml LB broth containing 100 μg/ml ampicillin and 12.5 μg/ml tetracycline for overnight at 37° C. Small scale plasmid DNA was isolated using standard alkaline lysis method. The isolated plasmid DNA was characterized by NotI or SfiI restriction endonuclease digestion. The result of a typical cloning experiment is shown in Table 3.

TABLE 3

| pRGR2Ap[a] (vector used in ligation) | PCR fragment (polymerase used) | colonies/ml transformation mix[b] | positive clones/ analyzed clones[c] |
|---|---|---|---|
| 50 ng | 2 μl (Taq DNA polymerase) | 340 | 9/9 |

TABLE 3-continued

| pRGR2Ap[a] (vector used in ligation) | PCR fragment (polymerase used) | colonies/ml transformation mix[b] | positive clones/ analyzed clones[c] |
|---|---|---|---|
| 50 ng | 2 µl (Pfu DNA polymerase) | 1170 | 9/9 |
| 50 ng | — | 5 | — |

[a]The positive selection vector pRGR2Ap was digested with Pml I restriction enzyme, and after heat inactivation of Pml I the vector DNA was used in ligation.
[b]Transformants were grown in presence of 100 µg/ml ampicillin and 12.5 µg/ml tetracycline.
[c]The plasmids from the transformants were digested with either Not I or Sfi I releasing the insert.

As expected, the Table 3 shows that the vector pRGR2Ap is capable of cloning the PCR fragments carrying 5'-TGGTAA-3' at its 5' end as produced by primers LC1261RGRF and LC1680R. Table 3 also shows that the vector pRGR2Ap is capable of cloning both types of PCR products produced by Taq and Pfu DNA polymerases. However, fewer number of clones are obtained in case of cloning of the PCR products obtained by Taq DNA polymerase because in such case only those PCR products of Taq DNA polymerase are ligated which have no dAMP overhang. Improved efficiency of cloning of the PCR products generated with Taq DNA polymerase could be achieved by treating the PCR products with a DNA polymerase with 3'-5' proof-reading exonuclease activity (T4 DNA polymerase, Pfu DNA polymerase etc.) thus removing the overhang DAMP (Costa and Weiner, 1994, Nucl. Acids Res. 22, 2423). The result also shows that 100% of the analyzed clones carried the 420 bp insert, which confirms the positive selection capability of the vector pRGR2Ap. The results also indicate that the other mutations have minimum effect on the function of β-lactamase, and hence PmlI could be used as the unique cloning site. The DNA sequence and restriction sites around the cloning site PmlI is also shown in FIG. 6.

In conclusion, a strategy for developing a positive selection vector system based on reporter gene reconstruction has been established; and wherein such vectors pRGR1Ap and pRGR2Ap have been successfully used for direct cloning of PCR generated DNA fragments. Use of pRGR1Ap and pRGR2Ap also greatly reduces exonuclease-induced false positive clones in a cloning experiment.

We claim:

1. A cloning vector comprising:
    (a) an origin of replication;
    (b) a gene encoding a functionally inactive beta-lactamase; and
    (c) a cloning site;
        wherein the cloning site is positioned such that insertion of an appropriate nucleic acid at the cloning site converts the functionally inactive beta-lactamase into a functionally active beta-lactamase and places the inserted appropriate nucleic acid at a position that is 3' to the coding sequence of the functionally active beta-lactamase.

2. A cloning vector as claimed in claim 1, wherein the vector comprises a nucleic acid selected from the group consisting of: SEQ ID NO:1 and SEQ ID NO:2.

3. A cloning vector as claimed in claim 1, wherein the gene encoding a functionally inactive beta-lactamase is a bla gene of pBR322 and comprises a mutation at position 286 such that the codon at position 286 does not encode a tryptophan.

4. A cloning vector as claimed in claim 1, wherein the cloning site comprises the sequence 5'-CACGTG-3'.

5. A vector as claimed in claim 1, further comprising a selectable marker gene.

6. A vector as claimed in claim 1, wherein the origin of replication is selected from the group consisting of:
    (a) a prokaryotic origin of replication;
    (b) an eukaryotic origin of replication
    (c) a viral origin of replication;
    (d) a plasmid pUC origin of replication;
    (e) a plasmid pBR322 origin of replication;
    (f) a phage M13 origin of replication; and
    (g) a phage f1 origin of replication.

7. A vector as claimed in claim 1, wherein the cloning site is selected from the group consisting of:
    (a) a restriction enzyme cleavage site that is unique in said vector;
    (b) multiple restriction enzymes cleavage sites; and
    (c) a restriction enzyme cleavage site that is not unique in said vector.

8. A vector as claimed in claim 1, wherein the vector comprises a promoter selected from the group consisting of:
    (a) a phage promoter;
    (b) a viral promoter;
    (c) a T7 promoter;
    (d) a T3 promoter;
    (e) an SP6 promoter;
    (f) a prokaryotic promoter; and
    (g) an eukaryotic promoter.

9. A cloning vector as claimed in claim 3, wherein the codon at position 286 encodes a valine.

10. A vector as claimed in claim 5, wherein the selectable marker gene is selected from the group consisting of:
    (a) a gene that confers antibiotic resistance;
    (b) a gene that is essential for the growth of the host under certain conditions;
    (c) a gene that is essential for replication of the vector in the host cell;
    (d) a gene that is essential for propagation of the vector in the host cell;
    (e) a gene encoding a chromogenic enzyme; and
    (f) a gene encoding a fluorescent protein.

11. A vector as claimed in claim 10, wherein the gene encoding a chromogenic enzyme is a lacZ gene.

12. A kit for cloning, comprising an aliquot of a vector as claimed in claim 1.

13. A kit of claim 12, wherein the vector is linearized.

14. A kit of claim 12, further comprising an aliquot of a primer, wherein the primer comprises a sequence at the 5' end such that upon ligation with the vector, the inactive beta-lactamase gene is converted into a functionally active beta-lactamase gene, and wherein the sequence at the 5' end of the PCR primer is the sequence 5'-TGGTAA-3'.

15. A kit of claim 12 further comprising an additional item selected from the group consisting of:
(a) an aliquot of DNA ligase;
(b) an aliquot of T4 DNA polymerase;
(c) an aliquot of T4 polynucleotide kinase;
(d) an aliquot of dNTPs,
(e) an aliquot of compatible competent host cells, wherein the host cell is capable of replication of the recombinant vector upon transformation;
(f) an aliquot of a control target DNA, wherein the control target DNA is suitable for a control PCR reaction that generates a control product, and wherein the control product is suitable for ligation with the vector;
(g) an aliquot of a forward control primer and an aliquot of a reverse control primer; and
(h) an aliquot of a control plasmid, wherein the control plasmid is suitable for a control transformation.

16. The kit of claim 15, wherein the additional item is provided in a separate container from the vector.

17. The kit of claim 15, wherein a plurality of additional items are provided in a single separate container from the vector.

18. The kit of claim 15, wherein the additional item is provided in a single container with the vector.

19. The kit of claim 15, wherein a plurality of additional items are provided in a single container with the vector.

20. A vector selected from the group consisting of pRGR1Ap and pRGR2Ap.

21. A method of cloning of a PCR-generated DNA fragment, the method comprising:
(i) generating a PCR fragment using a primer comprising a sequence at the 5' end such that upon ligation with a vector of claim 1, the inactive beta-lactamase gene is converted into a functionally active beta-lactamase gene, and wherein the sequence at the 5' end of the PCR primer is the sequence 5'-TGGTAA-3';
(ii) ligating the PCR fragment into the vector at the cloning site to produce a ligated product;
(iii) transforming an appropriate bacterial host cell with the ligated product to produce a transformant;
(iv) selecting a recombinant transformant by growing the transformant in a medium containing an antibiotic, wherein bacterial host cells that contain a functional beta-lactamase gene are resistant to the antibiotic.

22. The method of claim 21, wherein the method additionally comprises linearizing the vector.

23. The method of claim 21, wherein ligating the PCR fragment into the vector comprises the use of an agent selected from the group consisting of:
(a) a ligase;
(b) a recombinase;
(c) a topoisomerase;
(d) a transposase; and
(e) an adaptor and/or a linker.

24. The method of claim 21, wherein the antibiotic is ampicillin.

25. The method of claim 22, wherein the cloning site is a PmlI restriction site, and wherein the vector is linearized by digestion with PmlI restriction endonuclease.

26. The method of claim 25, wherein the vector is selected from the group consisting of pRGR1Ap and pRGR2Ap.

27. A method for making a positive selection cloning vector, the method comprising:
a. introducing a change in the nucleic acid sequence of a functionally active gene selected from the group consisting of: a gene encoding a beta-galactosidase protein, a gene encoding a fluorescent protein and a gene encoding an antibiotic resistance protein, wherein the change in the nucleic acid sequence generates a cloning site near the 3'-end of the coding sequence of the functionally active gene; and
b. determining whether the change in the nucleic acid sequence converts the functionally active gene into a functionally inactive gene, wherein a functionally inactive gene generated by the change in the nucleic acid sequence is a functionally inactive gene for use in a positive selection cloning vector; and
c. placing the functionally inactive gene in a vector for use as a cloning vector.

28. The method of claim 27, wherein the functionally active gene is selected from the group consisting of: a gene encoding a beta-lactamase, a gene encoding a green fluorescent protein and a gene encoding a beta-galactosidase.

* * * * *

SEQUENCE LISTING

<160> NUMBER OF SEQ ID NOS: 11

<210> SEQ ID NO 1
<211> LENGTH: 165
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctaaagtata tatgagtaaa cttggtctga cagcggccgc ttaggccatc gatatcatat      60
ggcgccttat tcaattacta ttcaactatt attcaattac acgtgcttaa tcagtgaggc     120
gccgatatca gccatatgtc tatttcgttc atcgatagtt gcctg                     165

<210> SEQ ID NO 2
<211> LENGTH: 186
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctaaagtata tatgagtaaa cttggtctga cagcggccgc ttaggccatc gatatcatat      60
ggcgcctaat acgactcact atagttattc aattactatt caactattat tcaattacac    120
gtgcttaatc agtgaggcgc cgatatcagc catatgtcta tttcgttcat cgatagtagt    180
tgcctg                                                                186

<210> SEQ ID NO 3
<211> LENGTH: 72
<212> TYPE: DNA
<213> ORGANISM: Artificial Sequence
<220> FEATURE:
<223> OTHER INFORMATION: Description of Artificial Sequence: Primer

<400> SEQUENCE: 3

```
caattacacg tgcttaatca gtgaggcgcc gatatcagcc atatgtctat ttcgttcatc    60
gatagttgcc tg                                                       72
```

<210> SEQ ID NO 4
<211> LENGTH: 111
<212> TYPE: DNA
<213> ORGANISM: Artificial Sequence
<220> FEATURE:
<223> OTHER INFORMATION: Description of Artificial Sequence: Primer

<400> SEQUENCE: 4

```
attaagcacg tgtaattgaa taatagttga atagtaattg aataaggcgc catatgatat    60
cgatggccta agcggccgct gtcagaccaa gtttactcat atatacttta g            111
```

<210> SEQ ID NO 5
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 5

```
tggtaagctt gcggccgcaa aggccacaat ttcacacagg aaacagctat g             51
```

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 6

```
tttcatcaac attaaatgtg agcgagtaac                                    30
```

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 7

```
gtcgcaagat cttgaaagct tgcgctcttc cgcttcctcg ctcac                   45
```

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 8

```
ctgagcagat cttaatctag agttctgcca agggttggtt tgcgc                   45
```

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 9

```
-continued ggaagatcta agcttacgtc aaagcaacca tagtacgcgc cc                          42

<210> SEQ ID NO 10
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 10
ggaagatctc cataaaattg taaacgttaa tattttgtta aaattcgc                    48

<210> SEQ ID NO 11
<211> LENGTH: 129
<212> TYPE: DNA
<213> ORGANISM: Artificial Sequence
<220> FEATURE:
<223> OTHER INFORMATION: Description of Artificial Sequence: Primer

<400> SEQUENCE: 11
attaagcacg tgtaattgaa taatagttga atagtaattg aataactata gtgagtcgta       60
ttaggcgcca tatgatatcg atggccaaag cggccgctgt cagaccaagt ttactcatat      120
atactttag                                                              129
```